United States Patent [19]

Krzewki et al.

[11] Patent Number: 5,620,696
[45] Date of Patent: Apr. 15, 1997

[54] POLYURETHANE INSECTICIDAL EAR TAG AND METHOD OF USE

[75] Inventors: Rudolf J. Krzewki, St. Joseph; Stanley Ackers, Kansas City, both of Mo.

[73] Assignee: Fermenta Animal Health Company, Kansas City, Mo.

[21] Appl. No.: 288,598

[22] Filed: Aug. 10, 1994

Related U.S. Application Data

[63] Continuation-in-part of Ser. No. 24,905, Mar. 2, 1993, Pat. No. 5,342,619, which is a continuation of Ser. No. 841,836, Feb. 26, 1992, abandoned.

[51] Int. Cl.$^6$ ..................................................... A01N 25/10
[52] U.S. Cl. ........................... 424/411; 424/405; 424/419; 424/DIG. 10; 514/919; 523/103
[58] Field of Search ....................................... 424/411, 406, 424/405, 403, 408, 419; 514/84, 875, 876, 478, 529, 531, 734; 523/103, 122; 524/130–132, 590; 528/51; 119/156

[56] References Cited

U.S. PATENT DOCUMENTS

| | | | |
|---|---|---|---|
| 4,189,467 | 2/1980 | Von Bittera et al. | 424/14 |
| 4,380,598 | 4/1983 | Robeson et al. | 524/163 |
| 4,425,874 | 1/1984 | Child | 119/156 |
| 4,428,327 | 1/1984 | Steckel | 119/156 |
| 4,430,961 | 2/1984 | Steckel | 119/156 |
| 4,506,630 | 3/1985 | Hair | 119/156 |
| 4,562,794 | 1/1986 | Speckman | 119/156 |
| 5,237,000 | 8/1993 | Lausberg et al. | 525/64 |

FOREIGN PATENT DOCUMENTS 211830  12/1981  United Kingdom.

*Primary Examiner*—Neil S. Levy
*Attorney, Agent, or Firm*—Shook, Hardy & Bacon L.L.P.

[57] ABSTRACT

A polymeric device and method for the control of insects on animals is disclosed. The device is in the form of an ear tag or other shape which can be attached to an animal using known techniques. A unique polymer/insecticidal formulation is provided by combining an ectoparasiticidal active compound, such as one or more organophosphates, carbamates, pyrethroids and organochlorines, with a polyurethane polymer. The polymer is the reaction product of 4,4'-diphenylmethane diisocyanate, polytetramethylene glycol and 1,4-butanediol. By utilizing the particular polymers described, high loadings of insecticides are possible and the resulting product shows no tendency to exude insecticide during prolonged storage. The product made according to the invention can provide effective control of horn flies on cattle for six months or more utilizing a single ear tag or the like where it would take two tags constructed according to the prior art to achieve comparable results. The result is lower costs in product and labor, greater safety to an animal and workers and a lower quantity of residual product to dispose.

20 Claims, No Drawings

POLYURETHANE INSECTICIDAL EAR TAG AND METHOD OF USE

BACKGROUND OF THE INVENTION

This is a continuation-in-part of application Ser. No. 08/024,905 filed Mar. 2, 1993, now U.S. Pat. No. 5,342,619 which was a continuation of application Ser. No. 07/841,836 filed Feb. 26, 1992, now abandoned.

This invention relates generally to insecticidal protective devices for non-human domestic animals and, in particular, to a tag or other device formed from a polyurethane polymer having an ectoparasiticidal active compound within the polymer matrix.

It has long been known that devices such as ear tags impregnated with insecticide are an effective means for providing control of horn flies and other insects on domestic livestock, particularly cattle. The most common material for formulating insecticidal animal tags has heretofore been polyvinyl chloride. In recent years, concern from ecological and human safety viewpoints have been raised with regard to utilizing plasticized polyvinyl chloride on animals intended for human consumption. Also, since polyvinyl chloride must be plasticized to perform satisfactorily as a tag, the quantity of active insecticide which can be incorporated into the product is reduced in direct proportion to the quantity of plasticizer required.

Another disadvantage of present insecticidal tag formulating techniques is that the high loadings of plasticizer and insecticide cause the completed product to exude or "bleed" insecticide. This makes an unacceptable commercial product which requires special packaging to accommodate a relatively long shelf life, necessitates avoiding high temperatures in transport and storage, and demands special handling requirements when the product is removed from the package for application to an animal.

The use of various polyurethanes as a polymer matrix for insecticidal animal collars has been disclosed in U.S. Pat. No. 4,189,467 to von Bittera et al. Loadings of up to 25% by weight of an ectoparasiticidal carbamate in the polyurethane collar were described by von Bittera et al. While these loadings are generally acceptable for many intended applications, higher loadings would nonetheless be desirable in order to reduce the weight and size of the collar.

It has also been previously known to utilize polyurethane resins for forming identification (I.D.) tags for animals. It is further known to attach to a polyurethane I.D. tag a porous or semi-permeable membrane in the form of a cell for holding a reservoir of insecticide. These membranes are made of a variety of different polymers including polyurethane. Their construction is shown and described in U.S. Pat. No. 4,562,794. The purported advantage to utilizing such a membrane is to provide greater control over the uniformity of release rate of the insecticide and higher insecticide depletion than can be obtained when the insecticide is within the polymer matrix. Some of the polymers which have heretofore been utilized for tags of the type contemplated by the referenced patent would not, however, permit sufficiently high loadings of insecticide to achieve a satisfactory tag by blending directly with an ectoparasiticidal compound. Inherently, this known construction is costly to manufacture because of the complicated steps of forming and filling the cell as well as making the mechanical fastener for joining the cell to the tag. Also, there is a higher than desirable incidence of product failure because of the membranes being punctured while in use on animals.

SUMMARY OF THE INVENTION

It is therefore an object of the present invention to provide an insecticidal animal protective tag which will accommodate a higher degree of loading of the insecticidal compound than previously known tags, thereby enhancing the effectiveness of the tag and extending its useful life.

Another object of this invention is to provide an insecticidal animal protective tag and method of preparing same which minimizes insecticide bleeding, thereby improving the shelf life of the product while reducing the risk of contamination by humans handling the ear tags.

Another one of the objects of this invention is to minimize environmental and health concerns regarding insecticidal tag devices by utilizing a polymeric matrix which is generally recognized as being environmentally safe and non-threatening to humans and does not require the addition of potentially dangerous plasticizers.

It is also an object of this invention to provide a method of protecting animals from insects, which is more environmentally safe and presents fewer health risks than existing practices.

It is a further object of this invention to provide a single insecticide ear tag which is as effective as two prior art tags using the same active compound so that a single ear tag can be used to provide the same level of protection as two conventional tags.

It is a still further object of this invention to provide a device, such as an ear tag, having high loadings of an ectoparasiticidal component so that smaller and lighter tags can be used to provide insect control for smaller and younger animals such as sheep and calves which have an ear size which cannot support higher weight ear tags without causing undesirable physical changes to the ear.

These and other objects of the invention will be made clear or become apparent from the following specification and claims.

The foregoing objects are achieved by an insecticidal tag-like device comprising an ectoparasiticidal component that is blended with a polymer which is the reaction product of 4,4'-diphenylmethane diisocyanate, polytetramethylene glycol and 1,4-butanediol. The invention also encompasses a method of preparing such a device by combining the ectoparasiticidal composition with the afore-described polymer.

The invention further encompasses a method of protecting non-human domestic animals from ectoparasites by attaching to the animal a device, such as an ear tag, comprising an ectoparasiticidal effective quantity of an ectoparasiticidal compound within a polymer matrix which is the reaction product of 4,4'-diphenylmethane diisocyanate, polytetramethylene glycol and 1,4-butanediol.

In one aspect of the invention, the ectoparasiticidal component used in the devices comprises an organophosphate. In another aspect of the invention, the ectoparasiticidal component comprises one or more carbamates, pyrethroids, and organochlorines, including in combination with an organophosphate. Notably, high loadings of the ectoparasiticidal component can be achieved in the devices of the present invention, including loadings of up to 70% by weight based on the total weight of the device.

DETAILED DESCRIPTION OF THE PREFERRED EMBODIMENT

In accordance with the present invention, an insecticidal device is provided for use in protecting non-human domestic animals from ectoparasites. The device comprises an ectoparasiticidal active amount of a compound in association with a polyurethane resin.

The polyurethane resins which are useful in the present invention are polyurethane aromatic polyether elastomers, specifically the polymers which are the reaction product of 4,4'-diphenylmethane diisocyanate, polytetramethylene glycol and 1,4-butanediol. These resins generally conform to Chemical Abstracts Service Registry Number CAS 9018-04-6. Such polymers can be formed by polymerization of the diisocyanate with glycol according to the following reactions:

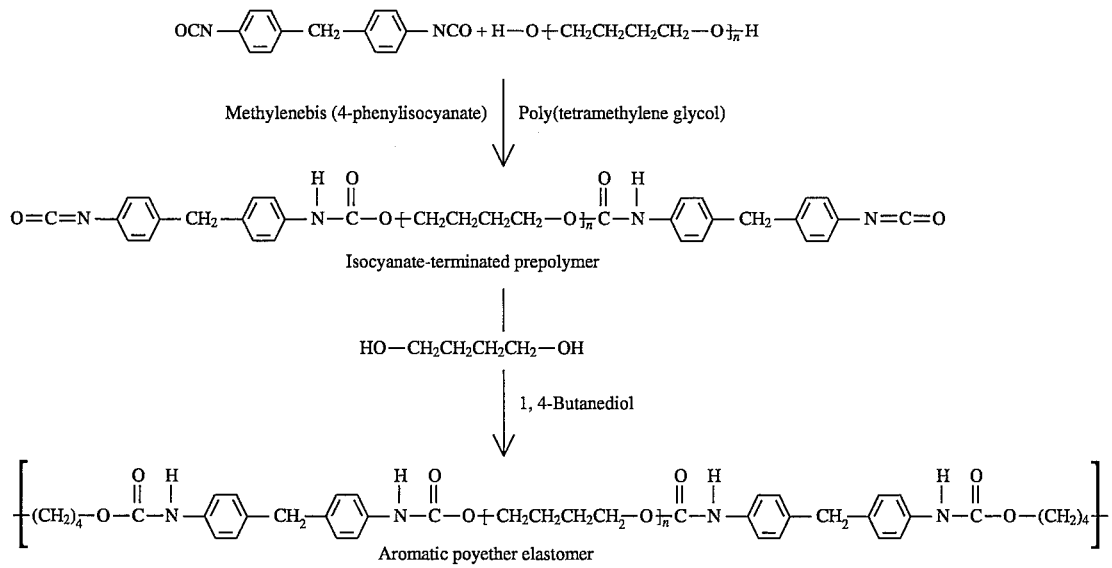

The moieties of the polymerization reaction will generally be present within the ranges of 20% to 40% diisocyanate, 50% to 70% glycol, and 2% to 10% butanediol (all by weight). It should be understood that the invention is not limited to ear tags and could take the form of a tail tag, ear clip, leg bracelet, collar, horse strip, medallion, chain tag or other device which could be attached to an animal. The final polymer will have a Shore hardness of 70–90 A units, a number average molecular weight which is not less than about 90,000, and a melting range within the range of about 70° C. to 190° C.

The following commercial resin products, all meeting the foregoing criteria, have been confirmed as satisfying the objectives of the invention and will be referred to hereinafter by the reference letters A through H:

| Reference Letter | Trademark | Manufacturer |
|---|---|---|
| A | Texin 985 A | Mobay Chemical Pittsburgh, PA USA |
| B | Morthane PE-90 | Morton Thiokol, Inc. Chicago, IL USA |
| C | Estane 98315 | B. F. Goodrich Co. Cleveland, OH USA |
| D | Morthane PE-50 | Morton Thiokol, Inc. Chicago, IL USA |
| E | Elastollan 1180A | BASF Corp. Parsippany, NJ USA |
| F | Pellethane 2103-80A | Dow Chemical Midland, MI USA |

-continued

| Reference Letter | Trademark | Manufacturer |
|---|---|---|
| G | Elastollan 1185A | BASF Corp. Parsippany, NJ USA |
| H | Pellethane 2103-70A | Dow Chemical Midland, MI USA |

Various insecticidal compositions, both liquids and solids, can be employed in association with the polymers described above. In one aspect of the invention, the active compound will preferably be an ectoparasiticidal active compound which is an organophosphate. Suitable organophosphate insecticides include O,O-diethyl O-2-isopropyl-6-methylpyrimidin-4-yl phosphorothioate, sold under the trademark Diazinon (Ciba-Geigy); S-1,2-bis(ethoxycarbonyl)ethyl O,O-dimethyl phosphorodithioate, commonly known as malathion; O,O-dimethyl O-4-nitro-m-tolyl phosphorothioate, sold under the trademark Sumithion by Sumitomo Chemical Co. Ltd,; and O,O,O ,O'-tetraethyl S,S'-methylene bis(phosphorodithioate), commonly known as ethion and sold by FMC, Inc.

In another aspect of the invention, the active component will preferably be an ectoparasiticidal active compound selected from the group consisting of one or more pyrethroids, organochlorines and carbamates.

The pyrethroid insecticides useful in the present invention include cyano(3-phenoxyphenyl)methyl 4-chloro-α-(1-methylethyl)benzeneacetate, commonly known as fenvalerate, and the active isomer thereof commonly known as esfenvalerate; cyano(3-phenoxyphenyl)methyl 3-(2,2-dichloroethenyl)-2,2-dimethylcyclopropanecarboxylate, commonly known as cypermethrin; (3-phenoxyphenyl)methyl 3-(2,2-dichloroethenyl)-2,2-dimethylcyclopropanecarboxylate, commonly known as permethrin; (3-phenoxyphenyl)methyl 2,2-dimethyl-3-(2-methyl-1-propenyl)cyclopropanecarboxylate, commonly known as phenothrine; cyano(4-fluoro-3-phenoxyphenyl)methyl 3-(2,2-dichloroethenyl)-2,2-dimethylcyclopropanecarboxylate, commonly known as cyfluthrin; [1α,3α(Z)]-(±)-cyano-(3-phenoxyphenyl)methyl 3-(2-chloro-3,3,3-trifluoro-1-propenyl)-2,2-dimethylcyclopropanecarboxylate, commonly known as cyhalothrine;

[1α(S*),3α(Z)]-(±)-cyano-(3-phenoxyphenyl)methyl 3-(2-chloro-3,3,3-trifluoro-1-propenyl)-2,2-dimethylcyclopropanecarboxylate, commonly known as lambda-cyhalotrin; cyano(3-phenoxyphenyl)methyl-2,2-dimethyl-3-(2-methyl-1-propenyl)cyclopropanecarboxylate, commonly known as cyphenothrin; (RS)-cyano-(3-phenoxyphenyl)methyl (S)-4-(difluoromethoxy)-α-(1-methylethyl)benzeneacetate, commonly known as flucythrinate; cyano (3-phenoxyphenyl)methyl 2,2-dimethyl-3-(1,2,2,2-tetrabromoethyl)cyclopropanecarboxylate, commonly known as tralomethrin; and [1α,3α(Z)]-(±)-(2-methyl[1,1'-bipheny]-3-yl)methyl 3-(2-chloro-3,3,3-trifluoro-1-propenyl)-2,2-dimethylcyclopropanecarboxylate, commonly known as bifenthrin.

The organochlorines useful in this invention include endosulfan, also known as C,C'-(1,4,5,6,7,7-hexachloro-8,9,10-trinorborn-5-en-2,3-ylene)(dimethyl sulfite) and methoxychlor, also known as 1,1,1,-trichloro-2,2-bis(4-methoxyphenyl)ethane.

The carbamates can include 2,3-dihydro-2,2-dimethylbenzofuran-7-yl methylcarbamate, commonly known as carbofuran; 2-isopropoxyphenyl methylcarbamate, commonly known as propoxur; 1-naphthyl methylcarbamate, commonly known as carbaryl; 2,3-isopropylidenedioxyphenyl methylcarbamate, commonly known as bendiocarb; and the like.

In a further embodiment of the invention, the active component will preferably be two or more ectoparasiticidal active compounds comprising an organophosphate in combination with one or more pyrethroids, organochlorines and carbamates. The organophosphates, pyrethroids, organochlorines and carbamates can include those compounds previously described.

To the extent that the ectoparasiticidal active compounds may exist as optical or geometric isomers, all isomers and racemic mixtures are understood to be included herein. All possible other isomeric forms of the compounds are also included herein.

The ectoparasiticidal active compound should be present in the device which is attached to the animal in an ectoparasiticidal effective quantity, normally at least approximately 20% by weight (based on final product) with levels up to approximately 70% by weight being acceptable. Thus, the polymer component will be present from 30% to 80% by weight of the final product. The ectoparasiticidal active compound, if liquid, may be introduced into the resin by a heating, absorption process, or if solid, it may first be dissolved in a volatile solvent, such as acetone, methyl ethyl ketone, methylene chloride and the like, followed by soaking in the polymer and removal of the solvent. Generally a blending time of thirty minutes in a high intensity mixer will produce a homogeneous, free flowing, polymer/insecticide mixture (called a "dry blend").

It is, of course, to be understood that ultraviolet light stabilizers such as 2-(2'-hydroxy-5'-methyl phenyl)-benzotriazole, fillers, lubricants, dyes, antioxidants such as octadecyl 3,5-di-tert-butyl-4-hydroxy-hydrocinnamate, pigments, and other inert ingredients may be incorporated into the formulation from zero to 2% by weight of the final product for serving their accepted functions which are well known to those skilled in the art. It has been found preferable to utilize up to 20% by weight polyvinyl chloride as a processing component to facilitate production of a free flowing dry blend. All of the foregoing optional substituents are generally added after the insecticide has been absorbed into the polymer. High intensity mixing for approximately five minutes is adequate to provide a homogeneous mixture incorporating the optional components.

The previously compounded dry blend may be formed into an acceptable shape, such as an ear tag, for attaching to an animal by various techniques well known to those skilled in the art. Extrusion, injection, and compression molding are all well known techniques, with injection molding being the preferred method of forming the preferred form of the device, namely, ear tags.

As a general process of preparing the components into a dry blend for molding processes, polyurethane beads or pellets are milled or ground to finer than approximately a 16 mesh size. The ground polyurethane is placed in a high intensity mixer and when the powder reaches a temperature of approximately 180° F., the ectoparasiticidal compound is added until completely absorbed over a five to seven minute period. The mixture is removed from the mixer and placed in a cooled ribbon blender. As the mixture cools, other and optional ingredients such as polyvinyl chloride, pigments, fillers, lubricants and antioxidants can be added. The resulting free-flowing powder can be processed and molded in a well known manner.

As an alternative to the molding techniques described above, the insecticidal device can be formed by coating the polyurethane resin, ectoparasiticidal active compound and optional additional components onto a substrate. The substrate is typically but not necessarily inactive and can be selected from any of various suitable materials such as porous or homogeneous plastic sheets, fabrics made of natural or synthetic fibers or combinations thereof, natural or synthetic leather, plastic mesh pattern cloths, coated fiberglass screening or cloth, and coated plastic screening. Substrates are typically used in those applications where added mechanical strength is needed for the final product because of very high loadings of the ectoparasiticidal compound in the polyurethane polymer matrix. It may also be desirable to use the higher mechanical strength substrates with comparatively lower loadings of ectoparasiticidal compound in those instances where high strength is necessary at the point of attachment of the device to the animal.

Among the various suitable processes which can be used for coating the substrates with the polymer and ectoparasiticidal compound are spread coating, dip coating and extrusion or coextrusion lamination techniques. As but one example, the polyurethane resin, ectoparasiticidal active compound and optional additional components can be dissolved in volatile polar solvents such as tetrahydrofuran, dimethyl formamide, dioxane, acetone, methyl ethyl ketone, chloroform and the like, or mixtures of such solvents. The solution is then applied to the appropriately shaped substrate using suitable knife coating, roller coating or transfer coating processes. The mixture can be applied to the substrate as a single layer or multiple layers with the solvents being removed from the product in drying ovens.

In dip coating processes, the substrate is cut to shape and is dipped into the solubilized mixture which has the desired flow properties to obtain a smooth coating and to diminish the tendency for the solution to drip from the substrate prior to drying. Following drying, the coated substrate can again be dipped into the mixture to build up the necessary coating thickness.

The substrates can also be coated by melting the polyurethane resin, ectoparasiticidal active compound and optional additional components in an extruder and forcing the melt through a slit die onto the substrate. The coated substrate can then be cooled on rollers followed by cutting into the desired shape of the final product such as an ear tag.

A preferred range for polymer and insecticide is 40% to 60% by weight polymer and 30% to 60% ectoparasiticidal active compound with the balance comprising polyvinyl chloride (up to 20% by weight) and up to 2% by weight inert ingredients such as antioxidants, ultraviolet light stabilizers and pigments, all well known to those skilled in the art (all weight percents based on final product).

The following examples are illustrative of some of the possible variations which are contemplated as being within the scope of the invention.

EXAMPLE 1

Various polymer compositions incorporating Diazinon insecticide were prepared according to the absorption procedure previously described utilizing technical grade (88% purity by weight) Diazinon and quantities within the preferred range. Ear tags were formed from the dry blend by injection molding.

Table I summarizes the composition formulations of the ear tags made according to this example.

TABLE I

Polyurethane Tags Made With Varying Quantities of Resin C and Diazinon Insecticide

| Lot No. | Composition, wt. % | | | | | |
|---|---|---|---|---|---|---|
| (minimum 200 tags) | 1 | 2 | 3 | 4 | 5 | 6 |
| Resin C | 49.4 | 51.3 | 50.8 | 48.8 | 52.6 | 48.5 |
| Diazinon (88%) | 38.3 | 46.1 | 43.1 | 43.9 | 44.0 | 43.7 |
| PVC | 12.3 | 2.6 | 5.1 | 6.1 | 0 | 6.0 |
| UV and antioxidant Stabilizers - (approx. 1:1 by weight) | — | — | — | 0.7 | 0.8 | 1.0 |
| Colorants, Pigments | — | — | 1.0 | 0.5 | 0.6 | 0.8 |
| Average Tag Weight (g) | 14.69 | 14.43 | 14.56 | 14.00 | 15.83 | 13.88 |

Table II provides a summary of the insecticide released during field trials utilizing the tags identified in Table I.

EXAMPLE 2

Various polymer compositions incorporating Diazinon insecticide were prepared according to the absorption procedure using technical grade (88% pure by weight) Diazinon and a dry blend was obtained. Ear tags were formed by injection molding. Table III summarizes the composition formulations of ear tags made according to this example.

TABLE III

Polyurethane Tags Made With Varying Quantities of Resins B, D, and F and Diazinon Insecticide

| Lot No. | Composition, wt. % | | | | |
|---|---|---|---|---|---|
| (minimum 200 tags) | 1 | 2 | 3 | 4 | 5 |
| Resin D | 53.9 | 42.4 | 51.7 | — | — |
| Resin B | — | — | — | 48.8 | — |
| Resin F | — | — | — | — | 48.4 |
| Diazinon (88%) | 45.8 | 57.3 | 46.5 | 43.9 | 43.5 |
| PVC | — | — | — | 6.1 | 6.0 |
| Stabilizers | — | — | 0.7 | 0.7 | 1.0 |
| Colorants, Pigments | 0.3 | 0.3 | 1.1 | 0.5 | 1.1 |
| Average Tag Weight (g) | 14.28 | 14.31 | 13.64 | 13.87 | 13.85 |

EXAMPLE 3

Ear tags from Lot 4 of Example 1 (Tables I and II) and from Lot 2 of Example 2 (Table III) were attached to the ears of cattle in herds located in New Mexico and Texas. One tag per animal was used to determine the efficacy against horn flies. In both trials, an untreated cattle herd was located within the vicinity of the tagged herd. On the application day, and weekly thereafter, horn fly counts were taken on at least ten randomly selected tagged and untagged animals. The results are summarized in Table V.

From this data it is evident that a surprising long term efficacy can be achieved with only one tag of the present composition, even under very high fly populations (infestation) for a period of at least six months.

TABLE II

Field Trials Average Release Rate of Diazinon For Tags From Table I

| Lot No. | 1 | | 2 | | | 3 | | 4 | | | 5 | 6 |
|---|---|---|---|---|---|---|---|---|---|---|---|---|
| Location | #1 | #2 | #1 | #3 | #2 | #1 | #1 | #4 | #2 | #3 | #1 | #1 |
| Application Date | 1-9-90 | 5-15-90 | 1-20-90 | 3-30-90 | 5-15-90 | 3-30-90 | 3-30-90 | 5-17-90 | 6-27-90 | 7-26-90 | 11-12-90 | 11-15-90 |
| Removal Date | 7-20-90 | 10-11-90 | 7-28-90 | 8-29-90 | 11-26-90 | 9-14-90 | 10-20-90 | 10-3-90 | 10-30-90 | 11-11-90 | 3-30-91 | 4-3-91 |
| Days on Cattle | 191 | 149 | 189 | 151 | 196 | 168 | 204 | 140 | 126 | 108 | 137 | 138 |
| Total Diazinon Released (g) | 2.757 | 3.604 | 4.162 | 4.359 | 4.259 | 4.083 | 3.812 | 3.920 | 3.289 | 2.696 | 3.191 | 2.471 |
| Average Release Rate mg/day | 14.4 | 24.2 | 22.0 | 28.9 | 21.7 | 24.3 | 18.7 | 28.0 | 26.1 | 25.0 | 23.3 | 17.9 |

TABLE V

Efficacy Trials - Control of Horn Flies Lot 4, Example 1; Lot 2, Example 2

| | Location: #1 | | | Location: #2 | | |
|---|---|---|---|---|---|---|
| | Treatment Date: 5-17-90 Average # of Flies per animal | | | Treatment Date: 4-7-90 Average # of Flies per animal | | |
| | Lot 4 Ex. 1 | Untagged Control | % Reduction | Lot 2 Ex. 2 | Untagged Control | % Reduction |
| # of Animals | 22 | 50 | | | | |
| | 35 | 50 | | | | |
| Pretreatment Count | 268 | 440 | | 800 | 800 | |
| # of Weeks | | | | | | |
| 1 | 22 | 498 | 96 | 90 | 800 | 89 |
| 2 | 14 | 484 | 97 | 150 | 800 | 81 |
| 3 | 4 | 668 | 99 | 100 | 900 | 89 |
| 4 | 5 | 630 | 99 | 20 | 750 | 97 |
| 5 | 9 | 618 | 99 | 12 | 500 | 98 |
| 6 | 4 | 396 | 99 | 10 | 500 | 98 |
| 7 | 3 | 452 | 99 | 10 | 400 | 98 |
| 8 | 6 | 602 | 99 | 6 | 300 | 98 |
| 9 | 30 | 750 | 96 | 10 | 200 | 95 |
| 10 | 26 | 1126 | 98 | 5 | 200 | 98 |
| 11 | 20 | 1166 | 98 | 6 | 200 | 97 |
| 12 | 22 | 1384 | 98 | 7 | 250 | 97 |
| 13 | 48 | 1038 | 95 | — | — | 97 |
| 14 | 64 | 984 | 93 | 20 | 250 | 92 |
| 15 | 38 | 1420 | 97 | 30 | 300 | 90 |
| 16 | 34 | 1106 | 97 | 10 | 300 | 97 |
| 17 | 5 | 706 | 99 | 40 | 300 | 87 |
| 18 | 24 | 594 | 96 | 14 | 350 | 96 |
| 19 | 36 | 610 | 94 | 20 | 300 | 93 |
| 20 | 164 | 540 | 70 | 30 | 300 | 90 |
| 21 | | | | 20 | 300 | 93 |
| 22 | | | | 25 | 300 | 92 |
| 23 | | | | 35 | 300 | 88 |
| 24 | | | | 30 | 200 | 85 |
| 25 | | | | 24 | 250 | 90 |

EXAMPLE 4

Ear tags containing 46 wt. % of a polyurethane resin, wt. % of technical grade Diazinon, 6 wt. % of PVC resin and 2 wt. % total of stabilizers, dyes, and pigments were prepared using the following resins previously identified:

| Tag Lot No. | Resin |
|---|---|
| 1 | A |
| 2 | B |
| 3 | C |
| 4 | D |
| 5 | E |
| 6 | F |

An efficacy trial with all tags was conducted in Alabama. As in Example 3, only one tag per animal head was employed, and an untagged control herd was kept in the vicinity of the tagged herds. An average number of horn flies from at least ten randomly selected animals in each herd, taken on the application date and every two weeks thereafter, are listed in Table VI.

TABLE VII

Efficacy Trials - Control of Horn Flies

Average Number of Horn Flies Per Animal

| Lot No. | 1 | 2 | 3 | 4 | 5 | 6 | Untagged Control |
|---|---|---|---|---|---|---|---|
| # of Animals | 30 | 32 | 63 | 40 | 40 | 35 | 25 |
| Pretreatment Fly Count treatment date 4-25-91 | 156 | 162 | 167 | 151 | 148 | 141 | 156 |
| # of Weeks | Post Treatment Count | | | | | | |
| 2 | 4.1 | 0.0 | 0.4 | 11.0 | 3.4 | 11.0 | 189 |
| 4 | 1.1 | 2.5 | 0.0 | 9.0 | 0.0 | 6.9 | 240 |
| 6 | 0.3 | 0.0 | 0.1 | 5.0 | 0.0 | 2.8 | 289 |
| 8 | 0.2 | 0.0 | 0.0 | 0.0 | 0.0 | 0.0 | 278 |
| 10 | 0.6 | 0.2 | 2.4 | 0.6 | 0.7 | 2.3 | 243 |
| 12 | 0.3 | 0.0 | 0.1 | 2.6 | 0.0 | 8.6 | 254 |
| 15 | 1.1 | 0.0 | 0.0 | 0.4 | 0.1 | 14.0 | 270 |
| 17 | 3.9 | 0.2 | 2.1 | 13.0 | 2.6 | 57.0 | 270 |

EXAMPLE 5

Using various techniques, insecticidal ear tags were prepared comprising various polyurethane resins and various pyrethroids. Table VII summarizes the composition formulations and Table VIII provides the preparation methods, number, and average weights for these tags.

TABLE VII

Tags Made With Varying Quantities of Polyurethane Resins and Insecticides

| Lot No. | Composition, wt. % | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Fenvalerate (95%) | — | 10.0 | — | — | — | 40.0 | — | — | — | 60.0 | — | — |
| Permethrin (95%) | — | — | — | 21.5 | — | — | — | — | 60.0 | — | — | 70.0 |
| Cypermethrin (86%) | 10.0 | — | 22.7 | — | 40.0 | — | 39.5 | 60.0 | — | — | 60.0 | — |
| Resin G | — | 87.0 | — | — | — | — | — | — | — | — | — | — |
| Resin C | — | — | 75.7 | 77.0 | — | — | 56.6 | — | — | — | — | — |
| Resin H | 87.0 | — | — | — | 58.8 | 40.0 | — | 35.8 | 38.6 | 38.6 | — | — |
| Resin E | — | — | — | — | — | — | — | — | — | — | 36.0 | 18.0 |
| PVC | — | — | — | — | — | 18.8 | 1.2 | — | — | — | — | 10.0 |
| UV and Antioxidant Stabilizers - (approx. 1:1 by weight) | 1.0 | 1.0 | 0.8 | 1.0 | 0.8 | 0.8 | 0.8 | 0.8 | 0.8 | 0.8 | 1.0 | 1.0 |
| Colorants, Pigments, Lubricant | 2.0 | 2.0 | 0.8 | 0.5 | 0.4 | 0.4 | 1.9 | 3.4 | 0.6 | 0.6 | 3.0 | 1.0 |

TABLE VIII

Pyrethroid Ear Tags

| Lot No. | Tag Preparation | Number of Tags Made | Average Weight (g) |
|---|---|---|---|
| 1 | Injection Molded | 56 | 14.44 |
| 3 | Injection Molded, three size | 132 | 5.11 |
| | | 106 | 9.90 |
| | | 160 | 15.10 |
| 4 | Injection Molded | 240 | 10.27 |
| 5 | Injection Molded | 150 | 4.75 |
| 7 | Injection Molded | 143 | 10.02 |
| 2,6,3,9,10 | Ear tags were cut out with with a cutting die from 0.085–0.090 inch thick compression molded plaques | 15 | 11.7–13.5 |
| 11 and 12 | Inactive placebo tag used as a carrier of the active compound. 4.8 g of the active compound was coating on the surface of placebo tags by dipping into a very viscous tetrahydrofuran solution of the formulations followed by evaporation of the solvent. | 60 | |

EXAMPLE 6

Ear tags from Lots 3, 4, 11 and 7 were compared with a commercial ear tag available from Fermenta Animal Health Company under the trademark Ectrin and containing 8% by weight fenvalerate in a PVC matrix and utilizing 28% by weight di-2-ethylhexyl adipate as a plasticizer. The tags were attached to ears of cattle in herds located in Texas. Two tags per animal were used to determine the efficacy against horn flies using the testing procedures previously described. The results are summarized in Table IX and demonstrate that surprising long term efficacy was obtained with the pyrethroid/polyurethane tags.

TABLE IX

Efficacy Trials - Control of Horn Flies

Average Number of Horn Flies Per Animal

| Lot No. | 3 | 4 | 11 | 7 | 7* | Ectrin | Untagged Control |
|---|---|---|---|---|---|---|---|
| # of Animals | 24 | 25 | 20 | 23 | 20 | 50 | 22 |
| Pretreatment Fly Count | 900 | 800 | 700 | 800 | 800 | 700 | 800 |
| Treatment date | 4/09 | 4/10 | 4/10 | 4/09 | 4/09 | 4/09 | — |
| # of Weeks | Post Treatment Count | | | | | | |
| 1 | 60 | 200 | 20 | 6.0 | 10 | 150 | 1000 |
| 2 | 50 | 180 | 20 | 5.0 | 10 | 200 | 800 |
| 4 | 30 | 50 | 12 | 6.0 | 8.0 | 40 | 800 |

TABLE IX-continued

Efficacy Trials - Control of Horn Flies

Average Number of Horn Flies Per Animal

| Lot No. | 3 | 4 | 11 | 7 | 7* | Ectrin | Untagged Control |
|---|---|---|---|---|---|---|---|
| 5 | 36 | 50 | 12 | 8.0 | 10 | 50 | 800 |
| 6 | 40 | 30 | 8.0 | 14 | 0.4 | 50 | 500 |
| 7 | 20 | 22 | 4.0 | 12 | 4.0 | 16 | 450 |
| 8 | 26 | 20 | 6.0 | 8.0 | 2.0 | 20 | 400 |
| 9 | 20 | 20 | 6.0 | 12 | 4.0 | 20 | 300 |
| 10 | 0 | 80 | 0 | 0 | 0 | 0 | 250 |
| 11 | 8 | 50 | 0 | 0 | 0 | 0 | 230 |
| 12 | 6 | 40 | 2 | 2 | 2 | 0 | 200 |
| 13 | 6 | 20 | 0 | 0 | 0 | 0 | 180 |
| Tag Weight | 10 g | 10 g | 5 g | 10 g | 5 g | 10 g | — |

*Tags trimmed to 50% size by weight

EXAMPLE 7

Ear tags comprising endosulfan and polyurethane in amounts within the ranges previously described are prepared using compression molding techniques, also as previously described. The composition formulations for the tags are summarized in Table X below.

TABLE X

Polyurethane Tags Mades With Varying Quantities of Resin E and Endosulfan Insecticide

| | Composition, wt. % | |
|---|---|---|
| Lot No. | 1 | 2 |
| Resin E | 58.4 | 38.4 |
| Endosulfan (98.1%) | 40.0 | 60.0 |
| UV and antioxidant Stabilizers - (approx. 1:1 by weight) | 1.0 | 1.0 |
| Colorants, Pigments, Lubricant | 0.6 | 0.6 |

The method of preparing a device for protecting animals from insects according to the present invention comprises combining an ectoparasiticidal active component with a polymer which is the reaction product of 4,4'-diphenylmethane diisocyanate, polytetramethylene glycol and 1,4-butanediol, and then forming the combination into a device which is attachable to an animal, such as an ear tag. The resin and ectoparasiticidal compound are preferably combined by utilizing 30% to 80% by weight polymer and 20% to 70% by weight of the compound. The most preferred method utilizes approximately 30% to 60% by weight of the ectoparasiticidal compound, 40% to 60% by weight polymer, and up to about 20% by weight polyvinyl chloride with up to 2% by weight inert ingredients, such as anti-oxidants, UV stabilizers, and pigment.

The invention also encompasses a method of protecting non-human domestic animals from ectoparasites which comprises attaching to the animal a device formed from a polymer which is the reaction product of 4,4'-diphenylmethane diisocyanate, polytetramethylene glycol and 1,4-butanediol, which polymer has been mixed with up to 70% by weight of an ectoparasiticidal active compound. The preferred method utilizes the percent by weight ranges previously specified for the method of preparing the device according to the invention. All percentages are by weight based on the final product.

The ectoparasites which are controllable in accordance with the present invention include flies such as horn, face, stable and house flies; wingless flies known as keds which frequently are an ectoparasite for sheep; lice; fleas; ticks; mites; grubs and the like.

Among the animals which can be protected using the method of the invention are bovine, ovine and porcine animals, as well as other livestock such as horses and poultry and fur-producing animals such as mink and fox. It is to be understood that the invention is not limited to protection of the animals specified but can include other animals as well.

From the foregoing it is apparent that the device and methods of the present invention provide for a highly effective way of protecting domestic animals from insects such as horn flies for a prolonged period of time. The devices according to the present invention are able to support surprisingly high loadings of insecticides. Equally surprising is the fact that the devices remain dry without exudation of insecticide, even after prolonged storage at elevated temperatures. Also, notwithstanding the unusually high loading of insecticide, the tags remain flexible and strong for long retention on the animals being protected.

Because of the high loadings of ectoparasiticidal compound(s) which can be obtained in the devices of the present invention, smaller devices can be used to provide effective control of ectoparasites on animals. The use of smaller devices is particularly advantageous because it allows the devices to be worn by smaller and younger animals with less likelihood of undesirable physical changes in the animals. For example, smaller ear tags can be worn by calves and sheep without causing drooping of the ear of the animal or causing enlargement of the attachment opening in the ear with potential resulting loss of the ear tag. In addition, the smaller sizes obtainable for the devices allows a single device to be used for smaller animals and two or more devices used for larger animals or heavily infested areas. The smaller devices can thus be used for a wider range of applications, thereby allowing for production of a fewer number of standard sized devices instead of numerous different sizes of devices.

Having thus described the invention, what we claim is:

1. A device for protecting animals from insects, said device comprising:

30% to 80% by weight of a polyurethane polymer which is the reaction product of 20% to 40% by weight 4,4'-diphenylmethane diisocyanate, 50% to 70% by weight polytetramethylene glycol and 2% to 10% by weight 1,4-butanediol and has a number average molecular weight of not less than about 90,000, said polymer being formed into a shape for attachment to said animals; and 20% to 70% by weight of an ectoparasiticidal active compound absorbed into and releasable from said polymer and selected from the group consisting of pyrethroids, endosulfan and methoxychlor.

2. The device as set forth in claim 1, including up to 20% by weight polyvinyl chloride.

3. The device as set forth in claim 1, comprising 40% to 60% by weight polymer and 30% to 60% by weight ectoparasiticidal active compound.

4. The device as set forth in claim 1, comprising approximately 46% by weight polymer, approximately 46% by weight ectoparasiticidal active compound, approximately 6% by weight polyvinyl chloride and 2% by weight inert ingredients.

5. The device as set forth in claim 1, wherein said polymer has a Shore hardness of between 70 and 90 A units.

6. The device as set forth in claim 1, wherein said polymer is shaped to form an ear tag.

7. A device for protecting animals from insects, said device comprising:

30% to 80% by weight of a polyurethane polymer which is the reaction product of 20% to 40% by weight 4,4'-diphenylmethane diisocyanate, 50% to 70% by weight polytetramethylene glycol and 2% to 10% by weight 1,4-butanediol and has a number average molecular weight of not less than about 90,000, said polymer being formed into a shape for attachment to said animals; and 20% to 70% by weight of an ectoparasiticidal active component absorbed into and releasable from said polymer, said ectoparasiticidal active component being selected from two or more of the group consisting of organophosphates, pyrethroids, and organochlorines, wherein said organochlorines are selected from the group consisting of endosulfan and methoxychlor.

8. The device as set forth in claim 2, including up to 20% by weight polyvinyl chloride.

9. The device as set forth in claim 7, comprising 40% to 60% by weight polymer and 30% to 60% by weight ectoparasiticidal active component.

10. The device as set forth in claim 7, comprising approximately 46% by weight polymer, approximately 46% by weight ectoparasiticidal active component, approximately 6% by weight polyvinyl chloride and 2% by weight inert ingredients.

11. The device as set forth in claim 7, wherein said polymer has a Shore hardness of between 70 and 90 A units.

12. The device as set forth in claim 7, wherein said polymer is shaped to form an ear tag.

13. A method of protecting non-human domestic animals from insects, said method comprising attaching to the animal a device comprising:

30% to 80% by weight of a polyurethane polymer having a number average molecular weight of not less than about 90,000 and which is the reaction product of 20% to 40% by weight 4,4'-diphenylmethane diisocyanate, 50% to 70% by weight polytetramethylene glycol; and 2% to 10% by weight 1,4-butanediol and 20% to 70% by weight of an ectoparasiticidal active compound selected from the group consisting of pyrethroids, endosulfan and methoxychlor absorbed into and releasable from said polymer to protect said animal from insects.

14. The method as set forth in claim 13, wherein said device includes up to 20% by weight polyvinyl chloride.

15. The method as set forth in claim 13, wherein said device comprises 40% to 60% by weight polymer and 30% to 60% by weight ectoparasiticidal active compound.

16. The method as set forth in claim 13, wherein said polymer has a Shore hardness of between 70 and 90 A units.

17. The method as set forth in claim 13, wherein said device is an ear tag.

18. The method as set for the in claim 13, wherein said animal is a bovine or ovine animal.

19. The method as set forth in claim 13, wherein said animal is a porcine animal.

20. A device for protecting animals from insects, said device comprising:

30% to 80% by weight of a polyurethane polymer which is the reaction product of 20% to 40% by weight 4,4'-diphenylmethane diisocyanate, 50% to 70% by weight polyteramethylene glycol and 2% to 10% by weight 1,4-butanediol and has a number average molecular weight of not less than about 90,000, said polymer being formed into a shape for attachment to said animals; and 20% to 70% by weight of an ectoparasiticidal active compound which is a pyrethroid absorbed into and releasable from said polymer.

* * * * *

UNITED STATES PATENT AND TRADEMARK OFFICE
CERTIFICATE OF CORRECTION

PATENT NO. : 5,620,696
DATED : April 15, 1997
INVENTOR(S) : Rudolf J. Krzewki and Stanley Ackers It is certified that error appears in the above-indentified patent and that said Letters Patent is hereby corrected as shown below:

At column 15, line 20, please delete "2" and insert --7--.

Signed and Sealed this

Twenty-fifth Day of May, 1999

Attest:

Q. TODD DICKINSON

*Attesting Officer*    *Acting Commissioner of Patents and Trademarks*